United States Patent

Bernstein et al.

Patent Number: 5,846,011
Date of Patent: Dec. 8, 1998

[54] BOTTLE WITH BUILT-IN TELESCOPING APPLICATOR HEAD AND SPOUT FOR APPLYING FLUID TO A BODY

[75] Inventors: Melvin Bernstein, 714 Jeffrey Dr., Baldwin, N.Y. 11510; Richard Ross, South Richford, Vt.

[73] Assignee: Melvin Bernstein, Baldwin, N.Y.

[21] Appl. No.: 796,602

[22] Filed: Feb. 7, 1997

Related U.S. Application Data

[63] Continuation of Ser. No. 319,810, Oct. 7, 1994, abandoned.

[51] Int. Cl.$^6$ .................................................. A45D 34/00
[52] U.S. Cl. ................................. 401/205; 401/6; 401/23; 401/27; 401/136; 401/140; 401/196; 401/207
[58] Field of Search ..................................... 401/205, 207, 401/196, 6, 23, 27, 136, 140

[56] References Cited

U.S. PATENT DOCUMENTS

| | | | |
|---|---|---|---|
| 457,826 | 8/1891 | Meeker | 401/205 |
| 960,008 | 5/1910 | Evans et al. | 401/23 |
| 979,377 | 12/1910 | Campbell | 401/205 |
| 986,926 | 3/1911 | Mahler | 401/207 |
| 1,047,852 | 12/1912 | Strickland | 401/196 X |
| 1,473,925 | 11/1923 | Dryer . | |
| 1,797,676 | 3/1931 | Baker . | |
| 1,960,738 | 5/1934 | Giezentanner . | |
| 2,040,625 | 5/1936 | Myers . | |
| 2,119,646 | 6/1938 | Pidel . | |
| 3,106,741 | 10/1963 | Stoner | 401/183 |
| 3,133,310 | 5/1964 | Yorker et al. | 401/262 |
| 3,261,515 | 7/1966 | Luedtke | 401/205 M |
| 3,372,846 | 3/1968 | Berkus . | |
| 4,135,274 | 1/1979 | Freeman | 401/140 M |
| 4,461,406 | 7/1984 | Vannucci . | |
| 4,553,871 | 11/1985 | Niles | 401/205 X |
| 4,726,491 | 2/1988 | Moon . | |
| 4,961,661 | 10/1990 | Sutton et al. . | |

FOREIGN PATENT DOCUMENTS

| | | | |
|---|---|---|---|
| 104197 | 7/1966 | Denmark | 401/196 |
| 1420454 | 11/1965 | France | 401/205 |

*Primary Examiner*—Steven A. Bratlie
*Attorney, Agent, or Firm*—Frishauf, Holtz, Goodman, Langer & Chick

[57] ABSTRACT

A bottle (1) for storing a fluid and for applying the fluid to a human body comprises a container (2) having an opening; and an elongated rod member (11) having a longitudinal axis, the rod member (11) being located in the opening, and the rod member being slidable along its longitudinal axis relative to the container (2) and being sealed against the container (2) so that an inner end of the rod member (11) is located within the container (2) and an outer end of the rod member (11) is located outside the container (2). The rod member (11) has at least one duct (15) extending at least partially in the direction of the longitudinal axis of the rod member (11), the at least one duct (15) forming a fluid connection between an outlet at the outer end of the rod member (11) and an orifice that is situated within the container. An applicator (9) is mounted at the outer end of the rod member (11) and has an applicator member or pad (10) that is permeable for the fluid and which is in fluid communication with the outlet of the duct (15). An auxiliary spout (14) is provided. The user may selectively use the applicator member with the applicator pad or the auxiliary spout.

9 Claims, 13 Drawing Sheets

BOTTLE WITH BUILT-IN TELESCOPING APPLICATOR HEAD AND SPOUT FOR APPLYING FLUID TO A BODY

This application is continuation of application Ser. No. 08/319,810, filed Oct. 7, 1994 now abandoned.

FIELD OF THE INVENTION

This invention relates to a bottle which contains a fluid, such as a lotion (i.e., a suntan lotion, skin lotion), medication, or the like, the bottle having a built-in applicator and spout for applying the fluid to various body parts, especially to inaccessible body parts such as the back of a person. Also, some people have arthritis and cannot reach various parts of their body such as the lower portions of the feet, etc. The present invention is helpful for such people to apply such fluids, lotions, medications or the like to such difficult-to-reach body parts.

Hereinafter, the contents of the bottle will be referred to simply as a fluid, for ease of description.

BACKGROUND

Various containers, spouts, pullout spouts and applicator systems, such as those described below, are known.

U.S. Pat. No. 4,726,491 discloses a container having a pullout spout for pouring liquid such as transmission fluid and oil in a limited access filling opening which is provided on an automobile engine. The pullout spout is located within an opening of, and sealingly connected with, the container. The pullout spout is movable like a telescope between a fully retracted position where its outlet is within the opening of the container and a fully protruded position. The container opening as well as the pullout spout are provided with threads for threadably connecting a sealing cap. When attached, the sealing cap engages the pullout spout and the thread of the opening, to close the container opening to prevent leakage of the contents of the container.

U.S. Pat. No. 3,372,846 discloses a container having a pouring spout that is slidable and sealingly engaged within a bore of a tubular plug. The tubular plug is mounted removably on a boss of a respective opening of the container and carries a closure cap which covers the retracted spout and its outlet.

U.S. Pat. No. 2,040,625 discloses an oil container having a filling opening and a pullout spout mounted thereon. The opening of the container is provided with a plug comprising a bore and the pullout spout is movable and located therein. The pullout spout comprises a thin straight pipe which carries on its outer end a closing cap for plugging the pullout spout on its outlet when desired.

A similar container is known from U.S. Pat. No. 1,797,676 which discloses a container for oil or other fluids which are to be dispersed in small quantities. This container is provided with a pullout spout of the telescope type. The pullout spout comprises an outer pipe and a smaller diameter inner pipe. The inner pipe is provided with an enlarged head that rests upon the outer pipe and the main nozzle, respectively.

Another container with a telescope-like spout is disclosed by U.S. Pat. No. 1,473,925. This spout is fixed on an opening of a container and comprises a plurality of curved tube-shaped elements. The tube-shaped elements are fitted in one another and are secured against rotation. A curved elongated spout is formed when all elements are fully extended. The container opening and the outlet can be closed with a cap when all elements are fully retracted.

U.S. Pat. No. 4,461,406 discloses a container for dispensing small quantities of liquid into restricted spaces. The container is a metal can which optionally comprises a diaphragm at its base to aid in the expulsion of the fluid. A flexible delivery tube is positioned within the can and extends through an opening provided on the can and is closed by a tapered tube. A collar is provided at the inner end of the delivery tube, which collar serves as a seal when the tube is in the extended position. After cutting off the top of the tapered tube, the delivery tube can be drawn out, whereby a spout is formed. After use, the delivery tube is pushed back into the container. The opening of the container is closed by a cap that fits onto the tapered tube.

U.S. Pat. No. 4,961,661 discloses a fluid applicator appliance with an extendable handle for applying suntan lotion, body lotion, shampoo, or antiseptic to the human body. The fluid applicator comprises a cylindrical vessel provided at one of its ends with a fluid applicator. The fluid applicator is essentially a tube with a duct connected at one of its ends with the vessel, and provided at its other end with a fibrous pad assembly. A joint allowing fluid passage is located between the pad assembly and the tube. The tube is mounted on the vessel by means of a screw-on cap disposed between the vessel and the tube. The cap has a central bore that is aligned with the duct of the tube. A plug connected with the inner wall of the tube is provided within the duct, which plug closes the bore when the tube is tightly screwed onto the cap. The vessel is located in a tubular sleeve that can slide thereon. An abutment prohibits the sleeve from being detached from the vessel. In order to apply fluid to inaccessible body parts, the sleeve can be drawn out to serve as a handle.

Another device for dispensing liquids such as polish for shoes or furniture or dye is disclosed in U.S. Pat. No. 2,119,646. The liquid is stored in a container provided at the neck thereof with threads. A cap is provided with a pipe that extends away from the cap. The cap is formed like a threaded sleeve and can be fixed upon the neck of the container. The pipe is positively fixed on the cap in a bore provided therein and carries a swab of cotton at the distal end thereof. The swab is in fluid communication with the interior of the container by means of the pipe that extends at one side away from the cap.

U.S. Pat. No. 1,960,738 discloses a container with a valve-controlled spout attached thereon. The spout is provided on a threaded cap which is mounted on an opening of the container. The spout is essentially a straight tube comprising a valve therein. The valve is controlled by a thin rod extending coaxially through the tube. A handle is detachably mounted on the container at the bottom thereof, and the handle is situated on a side opposite to the opening.

SUMMARY OF THE INVENTION

It is an object of the present invention to provide an improved bottle which is adapted to apply fluid on a human body in a convenient way, and which is especially useful to apply fluid from the bottle to difficult-to-reach body parts.

It is a further object of the present invention to provide such a bottle which is easy to use, which is relatively easy to manufacture, and which can be easily closed in a leak-proof manner when desired.

A bottle for storing a fluid and for applying the fluid to a human body comprises a container having an opening; and an elongated rod member having a longitudinal axis, the rod member being located in the opening, and the rod member being slidable along its longitudinal axis relative to the container and being sealed against the container so that an inner end of the rod member is located within the container and an outer end of the rod member is located outside the container. The rod member has at least one duct extending at least partially in the direction of the longitudinal axis of the rod member, the at least one duct forming a fluid connection between an outlet at the outer end of the rod member and an orifice that is situated within the container. An applicator is mounted at the outer end of the rod member and has an applicator member or pad that is permeable for the fluid and which is in fluid communication with the outlet of the duct.

An auxiliary spout may be provided, and means to selectively use the applicator member or the auxiliary spout is also provided.

DETAILED DESCRIPTION

Figures 1, 2:
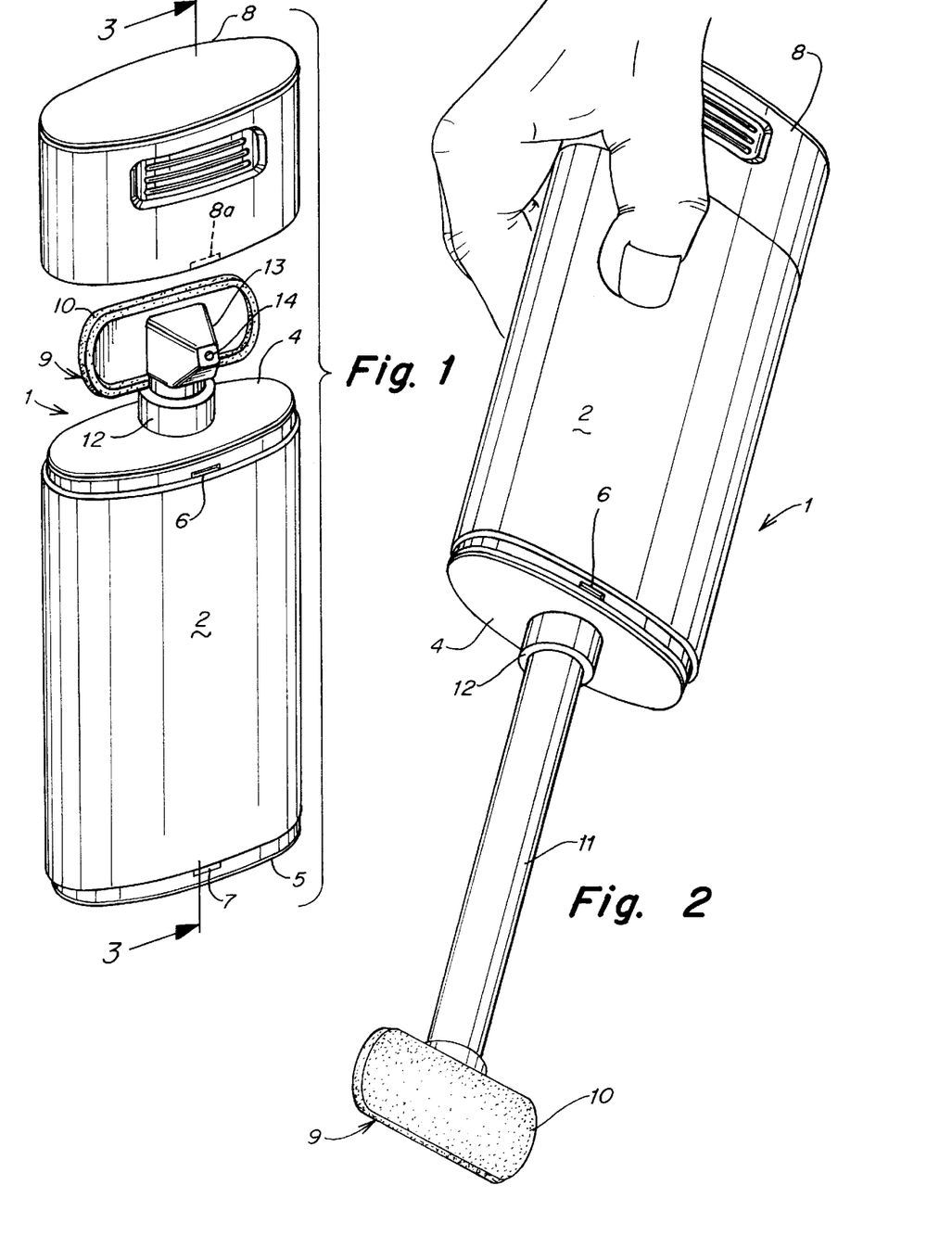
FIG. 1 is a perspective view of a bottle for applying fluid to a human body, which bottle comprises a combined applicator head and spout mounted on a telescope-like extendable hollow rod or tube member, shown in a retracted position.
FIG. 2 is a perspective view of the bottle of FIG. 1 with the rod or tube member in an extended position, ready for use.

As illustrated in FIGS. 1 and 2, a combined applicator and bottle 1 comprises a hand holdable container 2 with elliptical or oval cross section and having, a top end 4, and a bottom 5. The container 2 is made from a resilient or flexible material, such as plastic, and is filled with fluid which is to be applied to a human body. The container 2 is shown in the drawings as having an oval cross-section. The container 2 may, however, be round or have any other desired cross section, or may take any other desired shape. The top 4 as well as the bottom 5 of the container 2 are recessed and form grooves 6 and 7, respectively, which are arranged to receive a respective engaging parts 8a of a cap 8 and to carry the cap 8 (see FIGS. 3 and 4).

An applicator head 9 with a pad 10 for dispensing and applying fluid is provided at the top end 4 of the container 2 and is supported by a telescoping hollow rod or tube 11 (see FIG. 2). The telescoping rod or tube 11 is slidable and is sealingly received in a sleeve or neck 12 of the container 2, and provides fluid communication between the applicator head, 9 and the inner space of the container 2. The applicator head 9 is movable and can be pulled outwardly into an extended position, as illustrated in FIG. 2, and it can be thereafter pushed into the retracted position illustrated in FIG. 1. The cap 8 may be engaged on the bottom grooves 7 of the container 2 during use (see FIG. 2), thereby increasing the overall length of the whole bottle 1 when desired, especially when the head 9 is in the extended position, thereby facilitating application of the fluid to the body and also facilitating handling of the bottle during use.

Figures 3, 4:
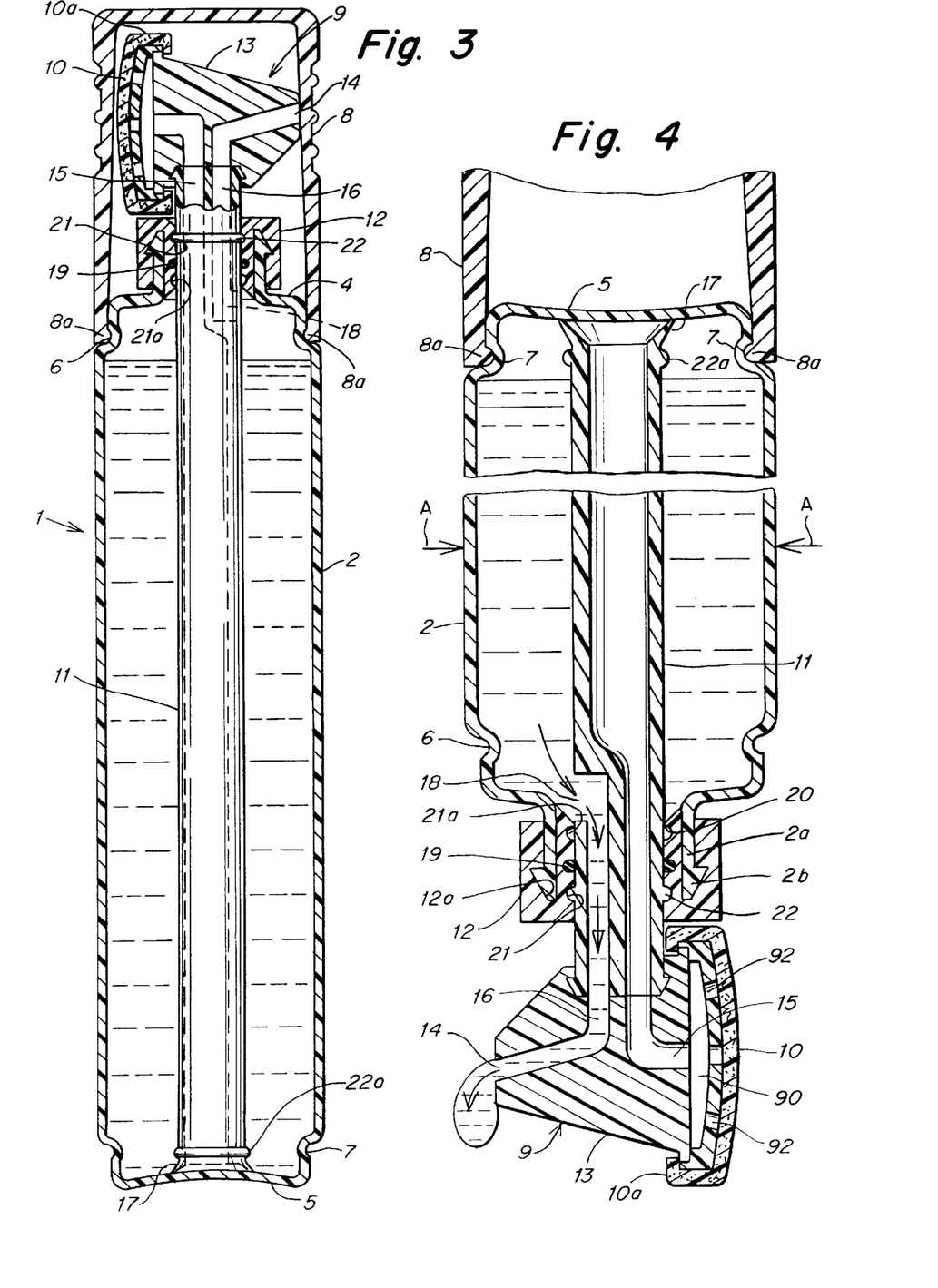
FIG. 3 is a longitudinal sectional view taken along line 3—3 in FIG. 1 of the bottle of FIG. 1 with the telescope-like rod or tube member in the retracted position and with the cover closed.
FIG. 4 is a longitudinal sectional view of the bottle of FIG. 1 in an upside down position and with the cap removed.

The movable (extendable) applicator head 9 comprises a body 13 with an apertured plate-like part carrying the pad 10 which is made of fabric, foam or any other material that is permeable to the fluid. Further, the applicator head 9 comprises a rear auxiliary dispensing opening 14 which is in fluid communication with the inner space of the container 2 and which can dispense fluid directly when the head 9 is in its most retracted position as shown in FIGS. 1, 3 and 4. This feature of dispensing fluid through opening 14 is explained below with reference to FIGS. 3 and 4.

As seen from FIGS. 3 and 4, two channels or ducts 15 and 16 are provided within the extendable rod or tube 11. The channel or duct 15 extends longitudinally through the rod or tube 11 and provides fluid communication between the pad 10 and the inner fluid-containing space of the container 2. The pad 10 is connected with an outlet of the duct 15 via a space 90 and holes 92 in the head 9. The duct 15 ends at the distal end of the rod or tube 11 in vicinity of the bottom 5 of the container 2. The distal end face of the rod or tube 11 is provided with a sealing portion 17 (preferably flexible) that abuts at the bottom 5 when the head 9 is in the most retracted position thereof, as shown in FIGS. 3 and 4. The fluid communication to the pad 10 (via channel 15) is then cut off and the pad 10 is effectively disabled. Moreover, the seal member 17 extends or flares outwardly at least a small distance away from the circumferential surface of the rod or tube 11 in a radial direction so as to also serve as a "stop" so that the rod or tube 11 cannot be inadvertently pulled out of the sleeve or neck 12 (see FIG. 5) of the container 2. Prevention of pulling-out of the rod or tube 11 from the neck 12 of the bottle can also be achieved by providing a bulge 22a on the end or lower (distal) end portion of the rod or tube 11 instead of or in addition to providing the outwardly flared seal member 17.

The duct 16 has an inlet port 18 in the vicinity of the sleeve or neck 12 so that the fluid dispensing opening 14 is in fluid communication with the inner space of the container 2 (via duct 16 and inlet port 18) when the applicator head 9 is in its retracted position (FIGS. 3 and 4). However, the fluid dispensing opening 14 is closed off by a respective part of the cap 8 which bears against opening 14 of the head 9 and closes opening 14 when the cap 8 is engaged on the bottle, as shown in FIG. 3.

Figures 5, 6:
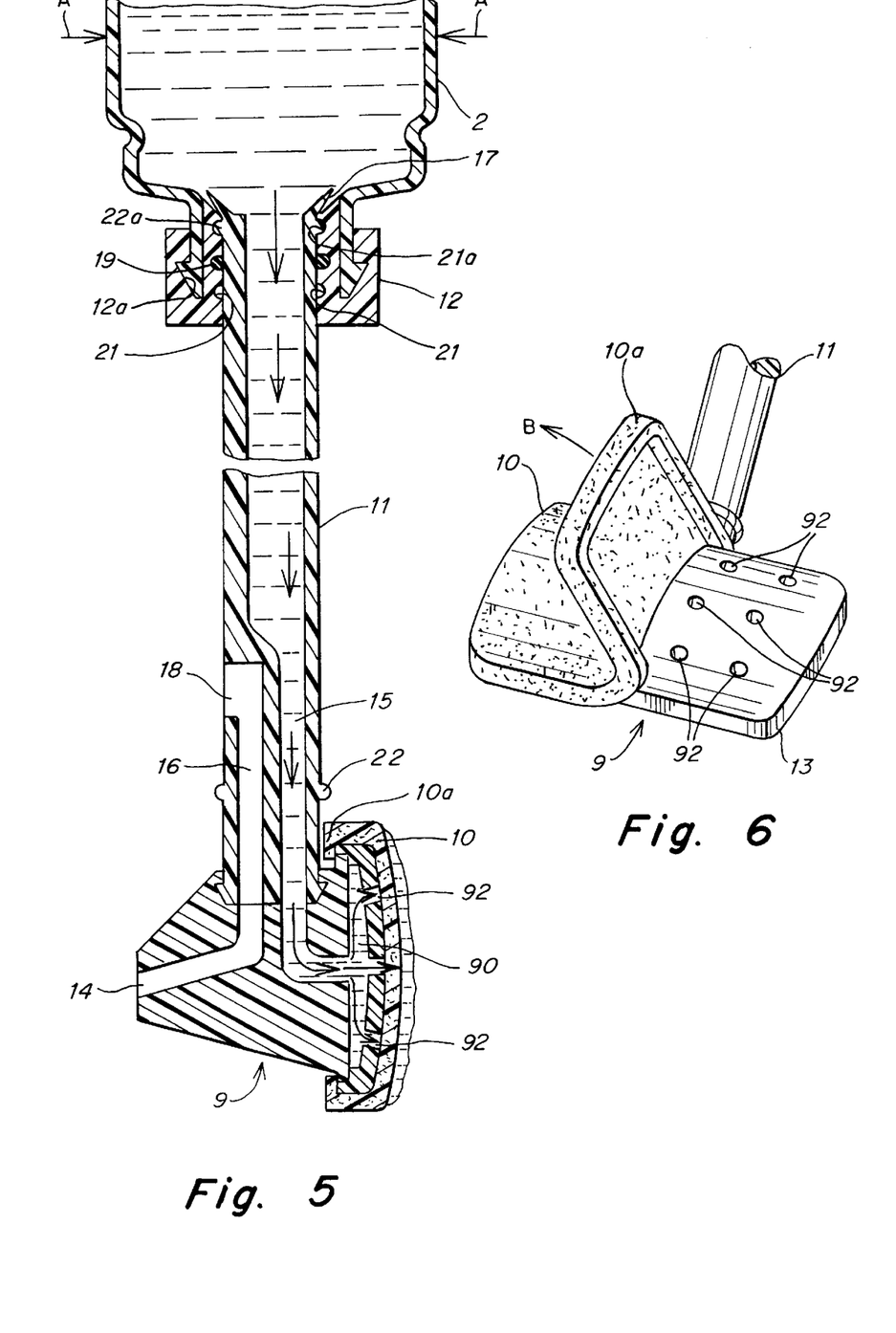
FIG. 5 is a view similar to FIG. 4 of the bottle of FIG. 1 with the hollow rod or tube member in an extended position.
FIG. 6 is a perspective view of the applicator head of the bottle of FIGS. 1–5 with a partially removed applicator pad.

Fluid can be dispensed via the dispensing opening 14 when the cap 8 is removed, when the head 10 is in the most retracted position, when the bottle 1 is held in the upside-down-position, and when the bottle is squeezed in the direction of the arrows A, as is shown in FIG. 4. However, the opening 14 is disabled when the rod or tube 11 is protruded or extended from the bottle, as shown in FIG. 5. When the rod or tube 11 is extended (see FIG. 5), the inlet port 18 is located outside of the container 2 (FIG. 5) and therefore, no fluid communication between the inner space of the container 2 and the dispensing opening 14 exists. As a result, the pad 10 is active for dispensing fluid when the head 9 is in the extended position of FIG. 5, and the dispensing opening 14 is active for dispensing fluid when the head 9 is in the most retracted position of FIGS. 3 and 4.

In order to prevent leakage between the rod or tube 11 and the sleeve or neck member 12, the neck member 12 comprises a sealing member 19 which is, as seen from FIG. 5, a resilient O-ring (for example made of rubber, plastic or the like) fitted in an annular groove provided within the neck member 12. It is also possible to form the sealing member in one part with the neck member 12 for example by forming an annular lip 20 (see FIG. 4) at the inner end of the neck member 12, which lip 20 is resilient and wipes against the outer surface of rod or tube 11 when it is pulled out to its extended position.

A detent assembly is provided by a recess, such as at least one annular groove 21, on the inner face of the sleeve or neck member 12 and by at least one protrusion 22 (such as an annular protrusion) provided on the circumferential surface of the rod or tube 11. The rod or tube 11 comprises a protrusion (annular protrusion) 22 at the end thereof closest to head 9, and a protrusion 22a at the distal end thereof so that the most retracted and the most protruded positions of rod or tube 11 are stable. A groove 21a is provided at the sleeve or neck member 12 between the sealing member 19 and the inside of the container 2, and the groove 21 is located on the sleeve or neck 12 at a position outwardly away from the sealing member 19. The protrusions 22, 22a and the grooves 21, 21a are preferably resilient so that the rod or tube 11 can be released from a detention position with a given axial force which is not so great as to make operation difficult by physically infirm persons. The protrusions 22, 22a are each preferably formed integrally with the rod or tube 11 as an annular bulge on the outer circumferential surface of the rod or tube 11.

In some cases only one protrusion at the inner end (or at the outer end) of the rod like member 11 may be sufficient.

As shown in FIGS. 3–6, the permeable, resilient pad 10 has a lip or surround portion 10a which extends over the rear end of the body part 13 of the applicator head 9. The pad 10 is preferably made of a resilient material and, due to the resiliency of the material thereof, remains engaged on the body part 13 of the head 9. The pad is easily removable by stretching it and pulling it off of the body part 13, for example, as shown by the arrow B in FIG. 6, and is replaced by engaging a new pad 10 over the body part 13.

The sleeve or neck member 12 is preferably a molded part having a recess 12a therein (see FIGS. 4 and 5). The portion of the container 2 having the opening therein has an upwardly extending portion 2a with a hook-like member 2b thereon which snappingly engages into the mating recess 12a of sleeve or neck member 12. The upper portion 2a, 2b of the container 2 is resiliently engaged with the neck member 12, which is preferably made of a resilient material which snaps over the hook-like portion 2b of the container 2. In this manner, after assembly, the sleeve or neck member 12 is locked in position and cannot be inadvertently removed.

Figures 7, 8:
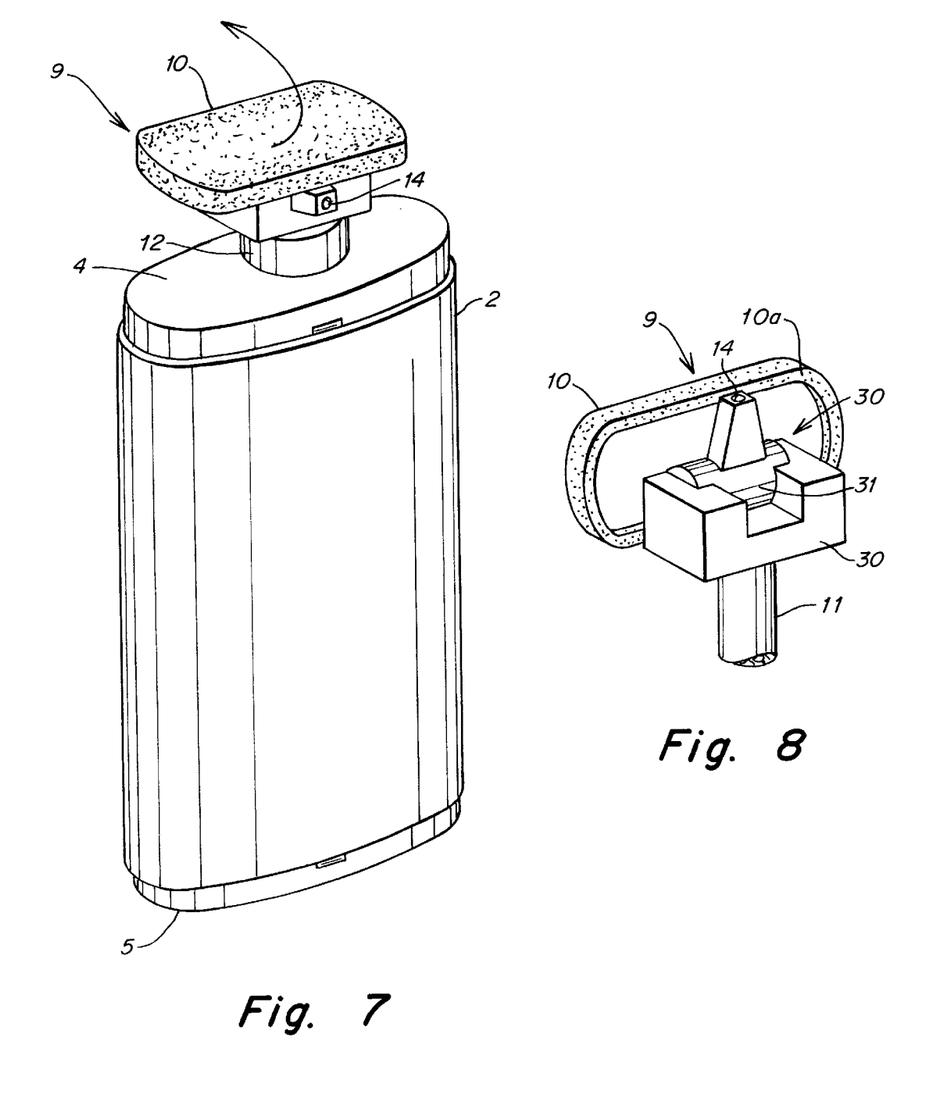
FIG. 7 is a perspective view of another bottle for applying fluid to a human body, which bottle is provided with an applicator head having a permeable applicator pad and an additional fluid dispensing opening or spout, wherein said applicator head is supported by a joint and is illustrated in a first dispensing position.
FIG. 8 is a perspective view of the applicator head of the bottle of FIG. 7 in a second dispensing position.
Figure 9:
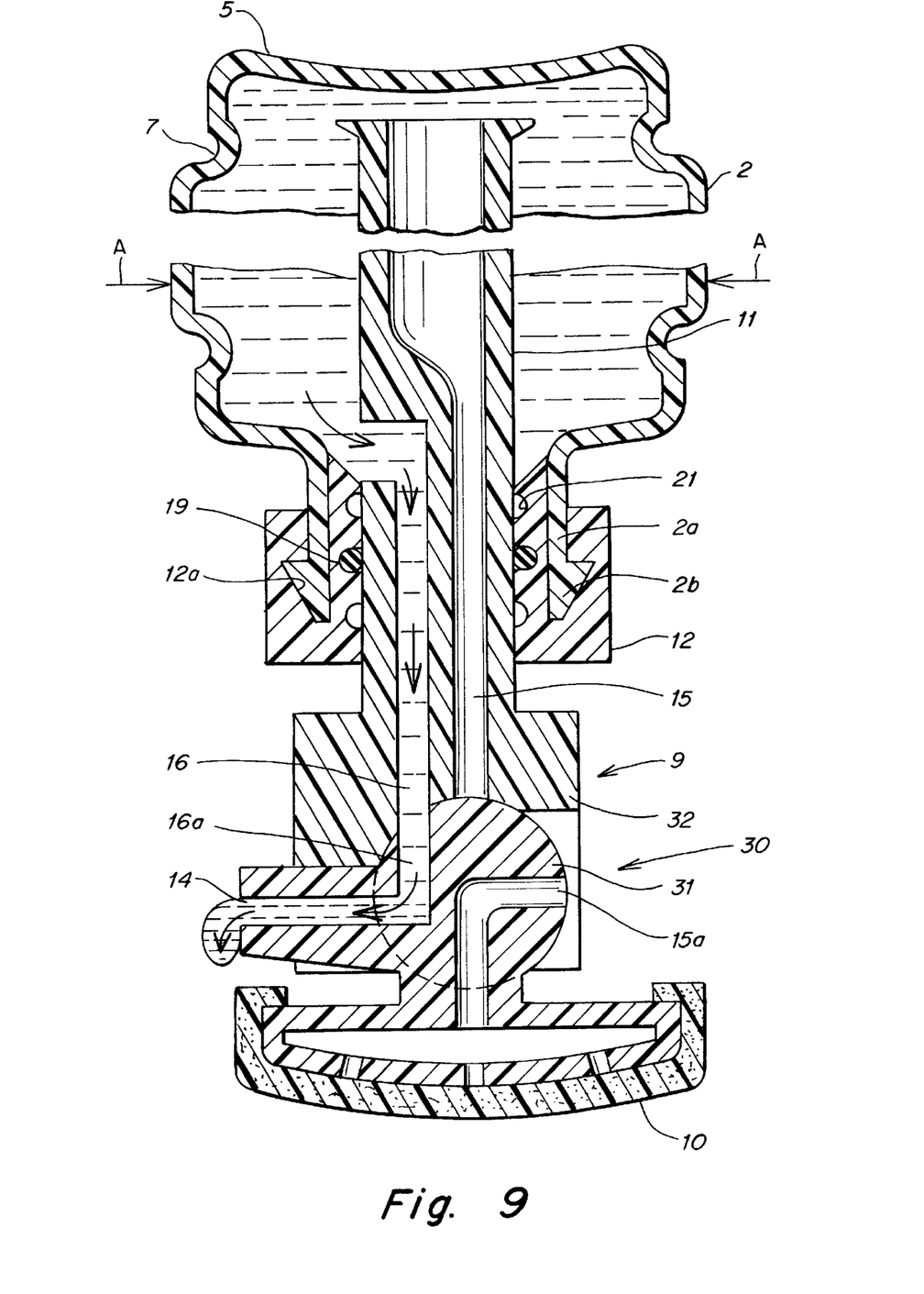
FIG. 9 is an enlarged longitudinal sectional view of the bottle of FIG. 7 and showing a valve formed by the joint and being in a first dispensing position where the applicator pad is disabled.
Figure 10:
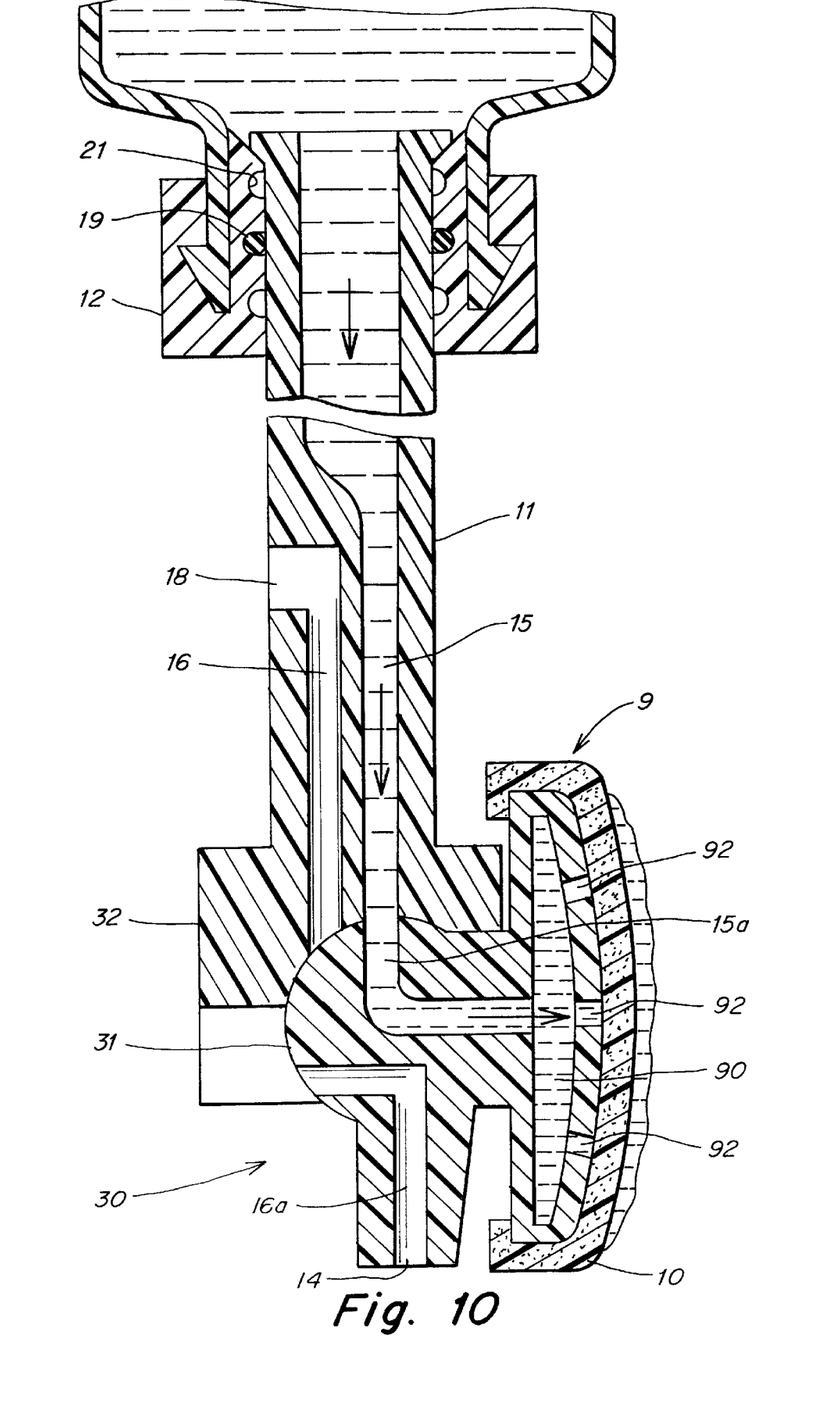
FIG. 10 is a detail of the bottle illustrated in FIG. 9 with the hollow rod or tube member in a most extended position and showing the valve formed by the joint in the second dispensing position where the dispensing opening or spout is disabled.

Another embodiment of the bottle according to the invention is shown in FIGS. 7 to 10. The bottle 1 of FIGS. 7–10 is generally similar to that described above. Therefore, the same reference numbers are used for comparable parts. FIGS. 7 and 8 illustrate the modified bottle having a joint 30 (see FIG. 8) connecting the head 9 and the rod or tube 11. The joint 30 is formed like a rotary hinge and defines a rotational axis that is arranged at a right angle to the axis of the rod or tube 11. As seen in FIGS. 9 and 10, a rotary valve member 31 is located within the rotary joint 30, which valve member 31 is controlled by the position of the head 9 relative to the rod or tube 11. The valve member 31 cooperates with mating valve member 32 at the end of tube or rod 11, and enables fluid communication between the inner space of the container 2 and either the pad 10 or the dispensing opening 14 through respective ducts 15, 16 provided within the rod or tube 11. The pad 10 is disabled and the dispensing opening 14 is enabled in the head dispensing position shown in FIGS. 7 and 9, whereas the pad 10 is enabled and the dispensing opening 14 is disabled in the pad dispensing position shown in FIGS. 8 and 10.

The inner structure of the valve 31 is shown in detail in FIGS. 9 and 10. The rod or tube 11 illustrated in FIGS. 9 and 10 has two ducts 15 and 16, as does the rod or tube 11 in the embodiment illustrated in FIGS. 1 to 6. As shown in FIG. 9, when the head 9 is rotated to the hand dispense position (that is, fluid is to be dispensed via opening 14), an internal channel 16a in valve member 31 communicates duct 16 with the opening 14, and permits dispensing of fluid from the container 2 when the container 2 is squeezed in a direction of arrows A in FIG. 9. In this position shown in FIG. 9, the pad is disabled. In the embodiment of FIGS. 7–10, it is not necessary for the bottom of the tube or rod 11 to extend to the very bottom of the container 2, and it is not necessary for the tube or rod 11 to seal against the bottom 5 of the container 2 when it is in its retracted position. This is because the valve member 31 effectively blocks off the duct 15 (pad dispensing duct) when the head 9 is in the position to dispense fluid via opening 14. This is why FIG. 9 shows a space between the bottom or interior end of the tube or rod 11 and the bottom 5 of the container 2.

FIG. 10 shows the bottle with the tube or rod 11 extended and with the head 9 rotated to the pad dispensing position. In the position shown in FIG. 10, the rotary valve member 31 is rotated to a position to block off the duct 16 and to communicate the duct 15 with the internal space 90 of the head 9 via an internal duct or passageway 15a.

Figure 11:
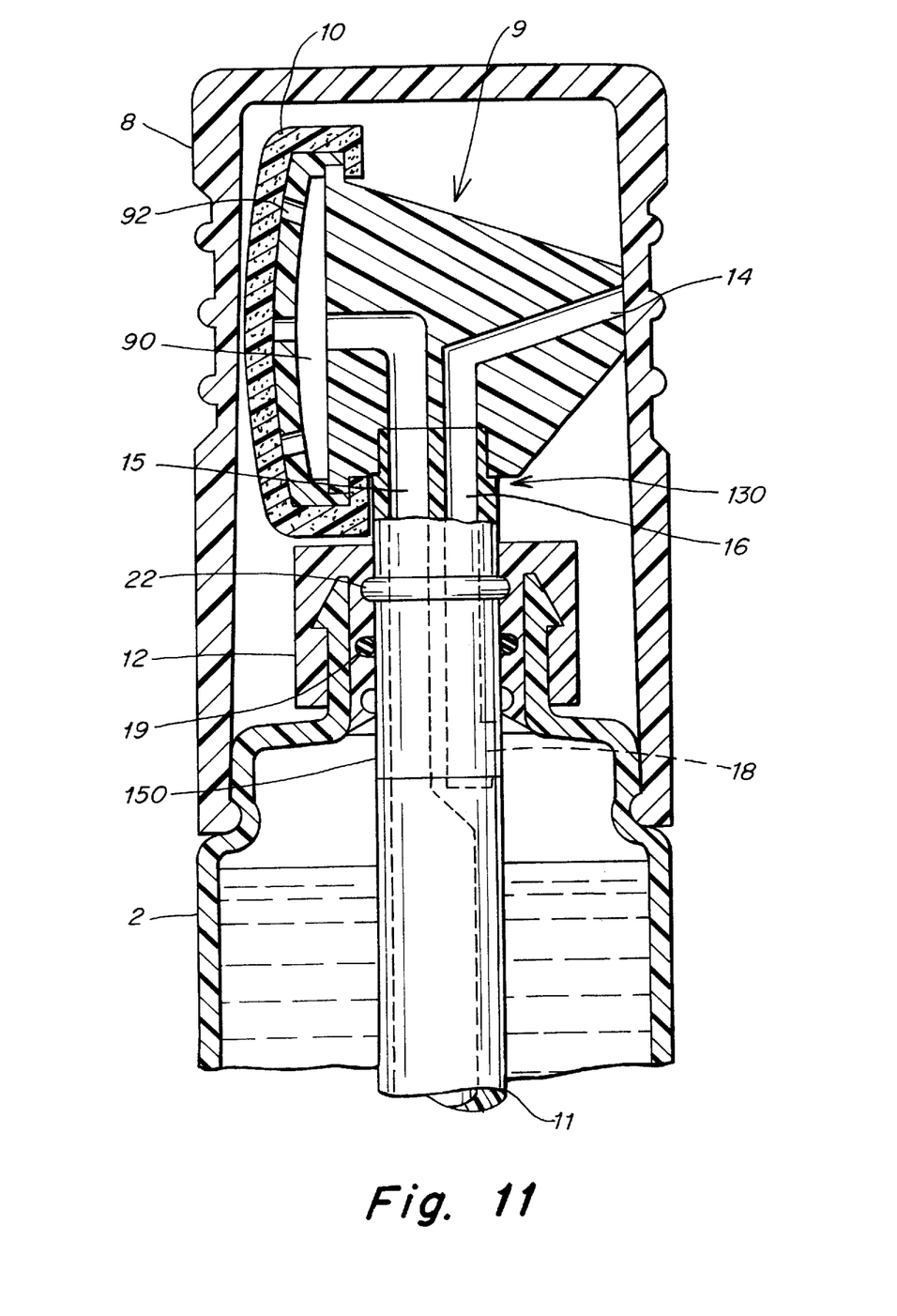
FIG. 11 is an enlarged longitudinal sectional view of a bottle according to the invention, which bottle is largely similar to the bottle illustrated in FIG. 3 but which shows in more detail how the head and tube could be fabricated.
Figure 12:
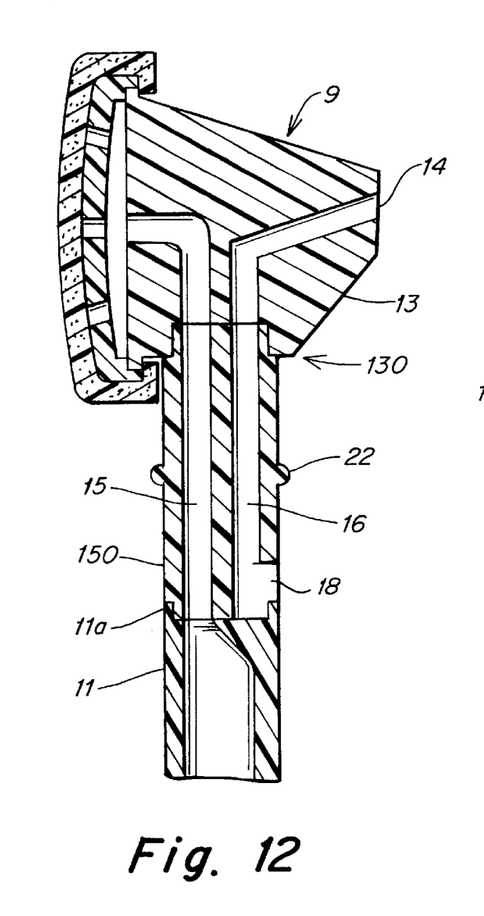
FIG. 12 is an enlarged longitudinal sectional view of the joint shown in FIG. 11.

The embodiment shown in FIGS. 1–6 can be of a modified structure and can define a structure having a rod or tube 11 construction, as illustrated in FIGS. 11 and 12. The joint 130 in FIG. 11 is formed between the head 9 and the rod or tube 11. The structure of the joint 130 is shown in detail in FIGS. 12, 12A and 12B. For preventing the rod or tube 11 from turning in the sleeve or neck member 12, it is sufficient that a frictional force exist between the sleeve or neck member 12 and the rod or tube 11. However, a means for preventing the rod or tube 11 from turning can be additionally provided. For example, a longitudinal groove (not shown) can be provided in the circumferential surface of the rod or tube 11 in a longitudinal direction, which is engaged with a protrusion or projection (not shown) provided on the inner surface of sleeve or neck member 12 and being in registration with the not shown groove, so that the rod or tube 11 is slidable longitudinally in sleeve or neck member 12, but is not rotational relative to sleeve or neck member 12.

Figure 12A:
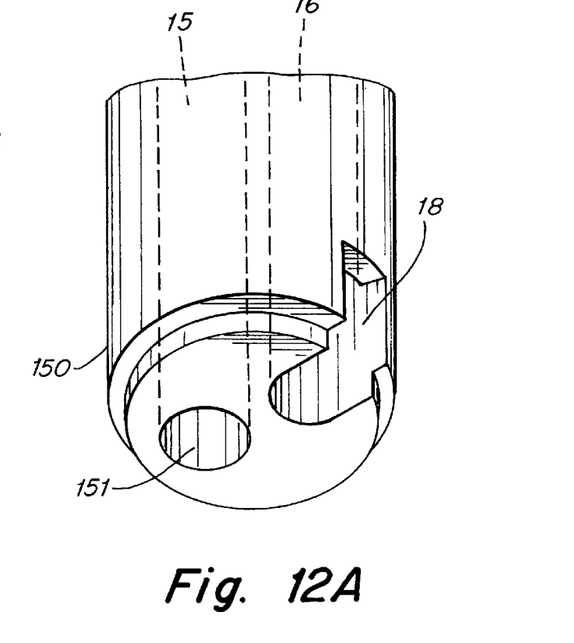
FIGS. 12A and 12B are exploded perspective views of parts of the joint shown in FIG. 12.
Figure 12B:
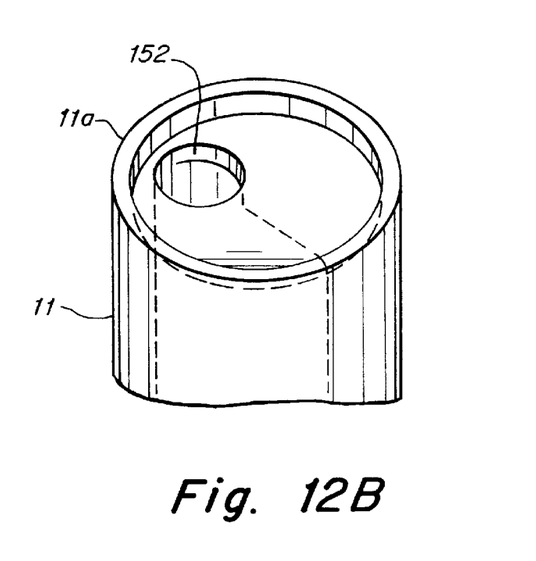

FIG. 12A shows an enlarged lower portion of an intermediate member 150 which can be used to fabricate the joint 130 between the rod 11 and the head 9. By providing a separately molded intermediate member 150 with two elongated ducts 15, 16 therein, manufacture of the rod member 11 is facilitated. The lower end of intermediate member 150 is shown in FIG. 12A and is preferably connected to an upper end 11a of rod member 11 (see FIG. 12B). The lower end of intermediate member 150 has a hole or opening 151 which is in registration with hole or opening 152 of rod member 11 (see FIG. 12B) when the intermediate member 150 is connected to the top 11a of rod 11. The intermediate member 150 is connected to the head member 9 at the upper end thereof, as shown in FIG. 12. The connections between the intermediate member 150 and the head 9 and rod 11 can be by snap fitting or by ultrasonic welding or by solvent, or by any other adhesive or mechanical interconnection to provide a liquid-tight connection. By providing the intermediate member 150, manufacture of the apparatus is simplified. The intermediate member 150 should be non-rotational relative to the rod 11 and head 9 to prevent misalignment of openings and channels.

Figure 13:
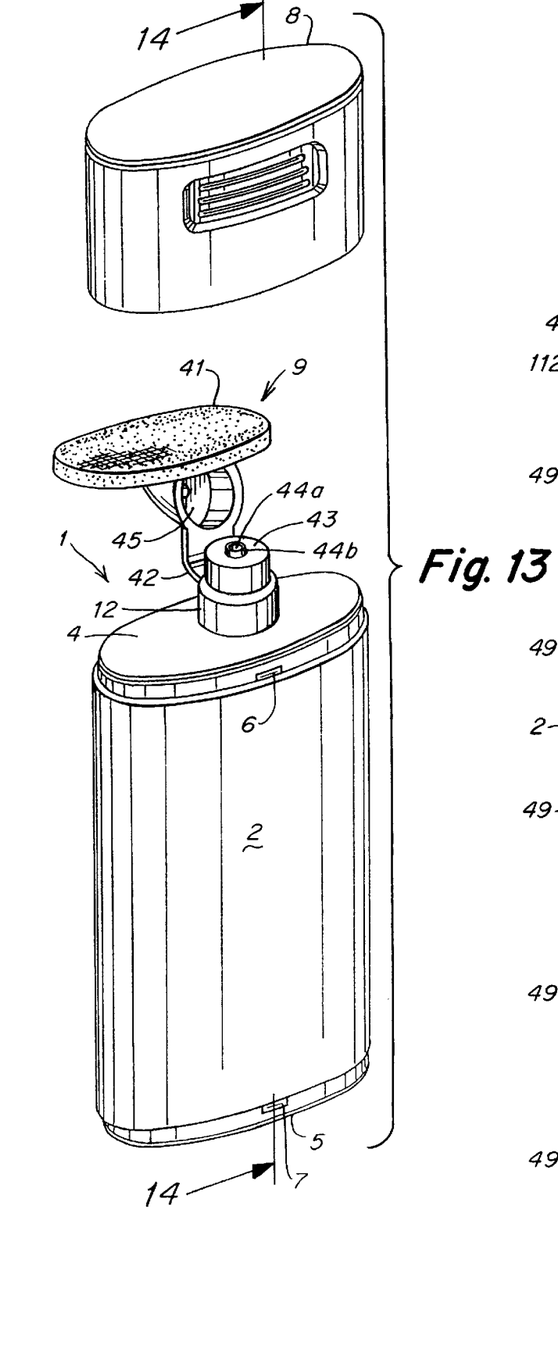
FIG. 13 is a perspective view of another embodiment of the bottle according to the invention, which bottle comprises an applicator head hinged at the end of a telescope-like hollow rod or tube with a living hinge.
Figure 14:
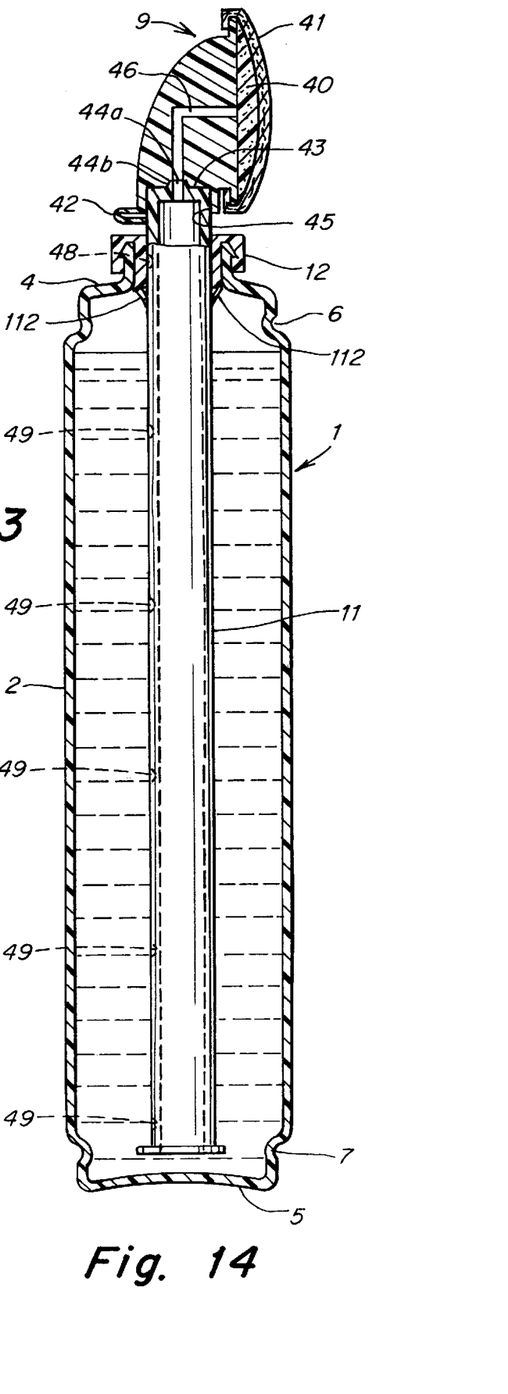
FIG. 14 is an enlarged longitudinal sectional view of the bottle illustrated in FIG. 13 taken along line 14—14 of FIG. 13 with the applicator head snapped onto the hollow rod or tube member.
Figure 15:
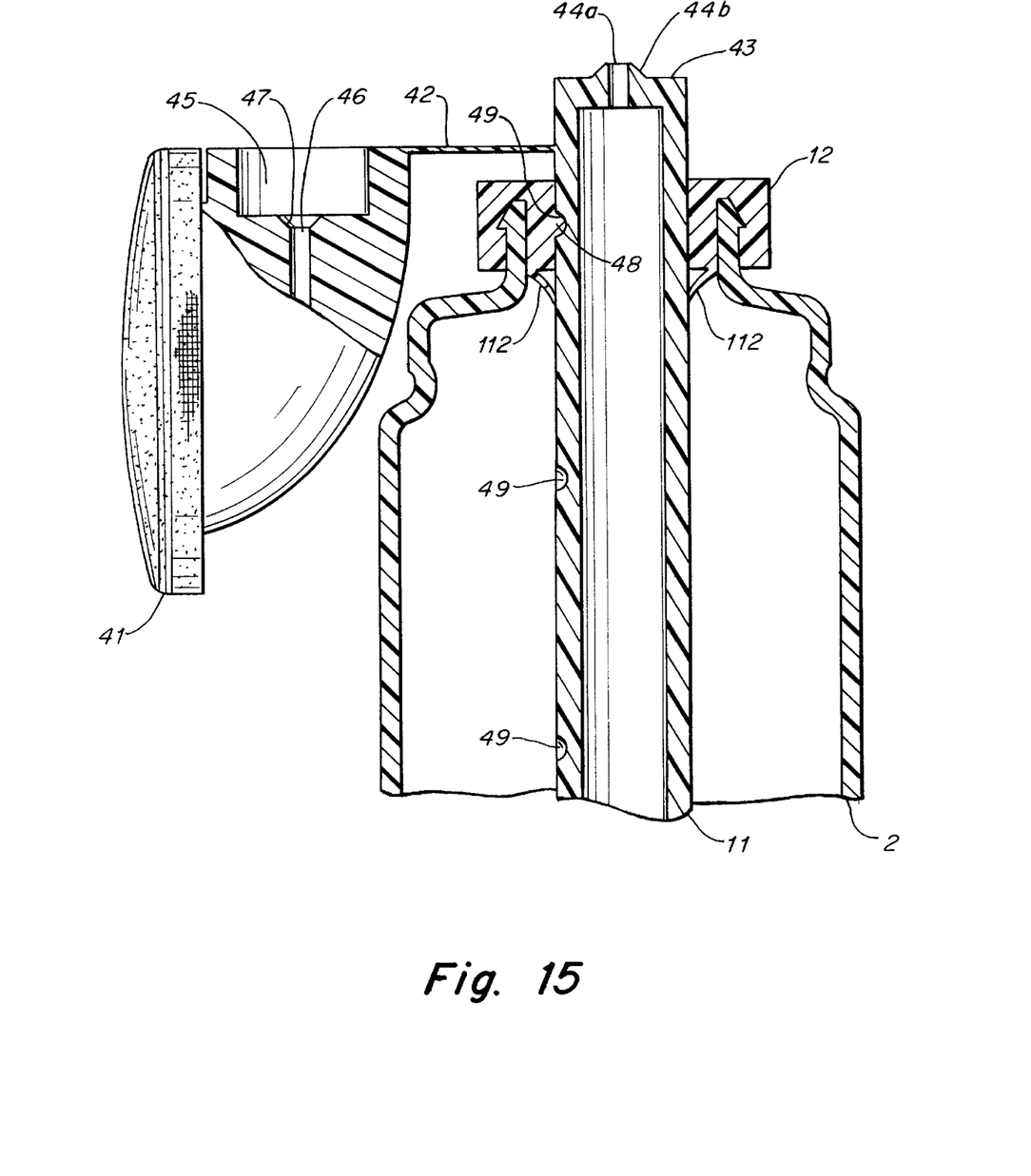
FIG. 15 is an enlarged longitudinal sectional view illustrating details of the bottle of FIG. 13 with the applicator head unsnapped or opened.

A further embodiment of the invention is shown in FIGS. 13–15. The bottle 1 comprises a container 2 with an extendable or telescoping rod 11 (having an axial duct or channel therein) similar to the above-described embodiments. The head 9 has a soft foam pad or distribution member 40 (see FIG. 14) covered by a soft cloth-like cover 41, instead of the one-piece pad 10 previously described. The head 9 is hinged to the rod or tube 11 by a living hinge 42 defining a hinge axis which is traverse to the axis of rod or tube 11. The rod or tube 11 has an essentially planar end face 43 with a dispensing opening 44a in the middle thereof. The opening 44a is at the top of a frustoconical part 44b provided at the end face 43. See FIG. 15

The head 9 is provided with a recess 45 at its side facing the end face 43 of the rod or tube 11, which recess 45 fits over (preferably tightly over to provide a seal) the upper part of the rod or tube 11 adjacent the end face 43. A channel 46 is provided within the head 9 that ends within the recess 45 with funnel-shaped portion 47 (FIG. 15) forming a sealing connection with the frustoconical part 44b. Channel 46 provides a fluid connection to the foam pad or distribution member 40. The frustoconical part 44b and the connection funnel portion 47 have mating surfaces that form a sealed connection when abutting each other.

When the head 9 is pivoted about living hinge 42 to the open position as shown in FIG. 13, the contents of the container 2 can be dispensed via opening 44a by squeezing the container 2, for hand application of the fluid. When the head 9 is pivoted to the closed position, shown in FIG. 14, the fluid from within the container can be dispensed via the distribution members 40, 41 of the head 9, with the telescoping rod either in the retracted position shown in FIG. 14, or in a fully or partially extended position relative to the container 2. In the embodiment of FIGS. 13 and 14, the rod member 11 preferably does not extend to the bottom 5 of the container 2 in the fully retracted position. See FIG. 14. Moreover, an integral wipe member 112 is preferably provided at the interior end of sleeve or neck member 11, to provide a seal against the outer surface of the telescoping rod 11. The wipe member 112 permits sliding movement of the rod member 11 relative to the neck member 12.

A detent mechanism is formed by a detention ball or projection 48 resiliently supported within the inner wall of the sleeve or neck member 12. Recesses 49 are provided along the length of the rod or tube 11 on the circumferential surface thereof. The recess 49 cooperate with the ball or projection 48, as shown in FIG. 15, so that the rod or tube 11 can be locked or retained at various positions relative to the container 2. The ball detent 48 can merely be a resilient integral projection made of the same plastic material as neck member 12.

Figure 16:
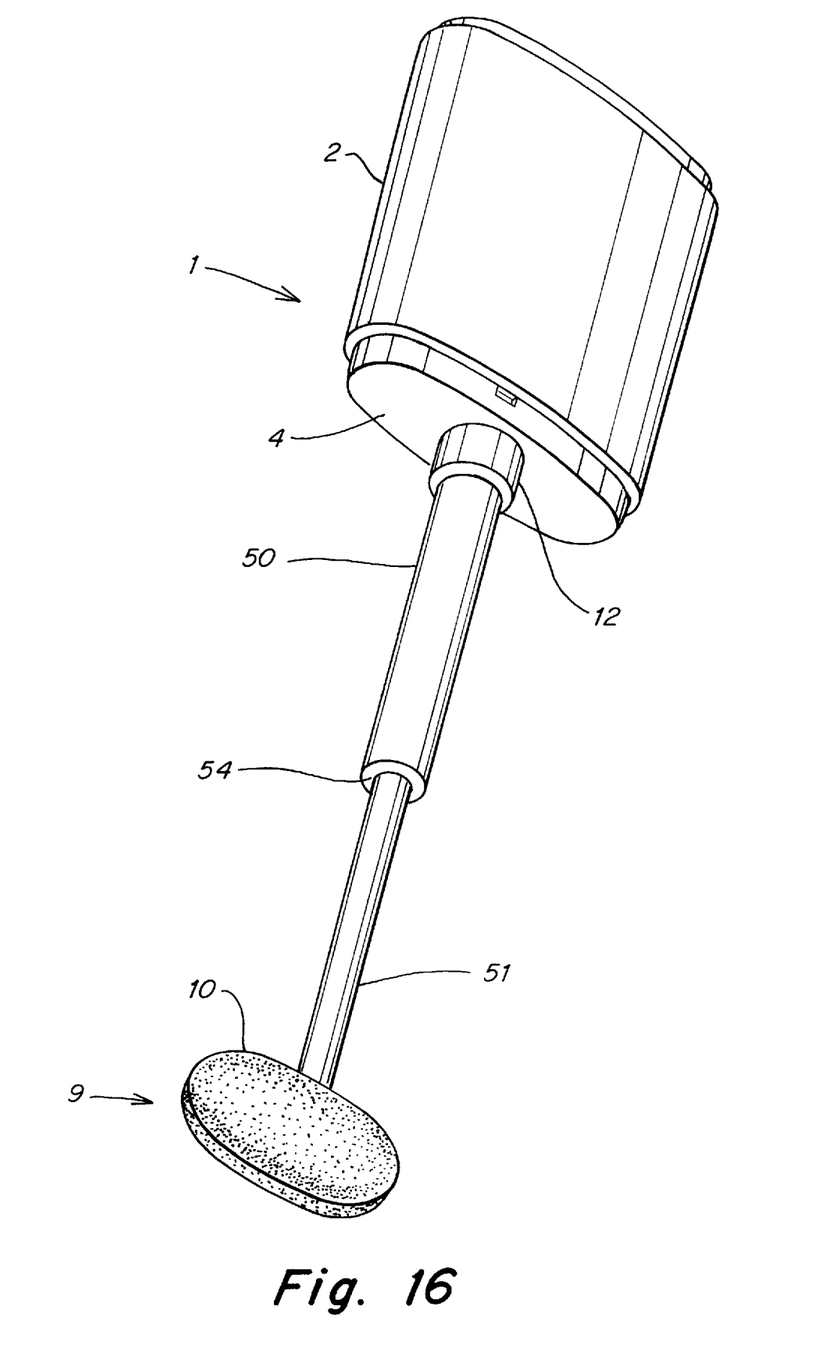
FIG. 16 is a perspective view of a further embodiment of the bottle according to the invention with a telescoping hollow rod or tube member comprising two telescoping segments.
Figure 17:
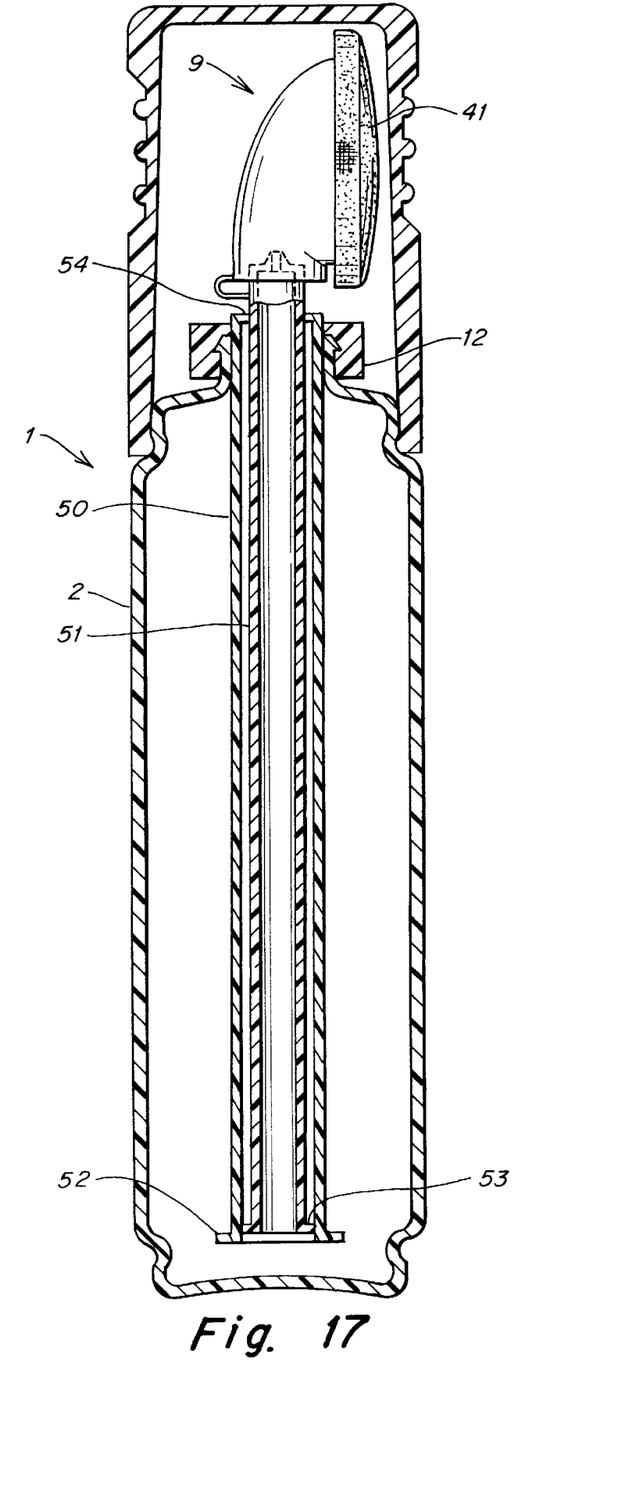
FIG. 17 is a longitudinal sectional view of the bottle illustrated in FIG. 16 with the telescoping segments in their retracted position and with the cap on the bottle.

A further modified embodiment is shown in FIGS. 16 and 17, and comprises a two-section telescope-like rod or tube. The rod comprises an outer tube 50 slidably guided by the sleeve or neck member 12 (similar to tube 11 of the above-described embodiments) and a telescoping inner tube 51 which is slidably mounted within the outer tube 50. This arrangement allows the bottle 1 to be made with either a very small container 2 having a small height, or enables the previously described containers to have a larger extension length of the rod or tube, depending on what is desired.

FIG. 16 shows the embodiment with the two-section telescoping rod extended, ready for application of fluid via the head 9 and pad 10. FIG. 17 shows a longitudinal sectional view of the embodiment of FIG. 16, but with the two-section telescoping rod or tube 50, 51 in its fully retracted position. In the embodiment shown in FIG. 7, the head arrangement shown in FIG. 15 is used. Other head arrangements, of course, could be used. The lower portion of outer tube 50 has a radially extending stop member or ridge 52 formed thereon to prevent the tube 50 from being pulled out of the container 2. Similarly, the lower end of rod or tube 11 of FIG. 14 is provided with such a stop member. The lower end of inner tube 51 has a radially extending stop member 53 thereon which cooperates with an inwardly extending projecting member 54 at the upper end of outer tube 50, to prevent the inner tube 51 from coming out of outer tube 50 when the telescoping member is extended.

Figure 18:
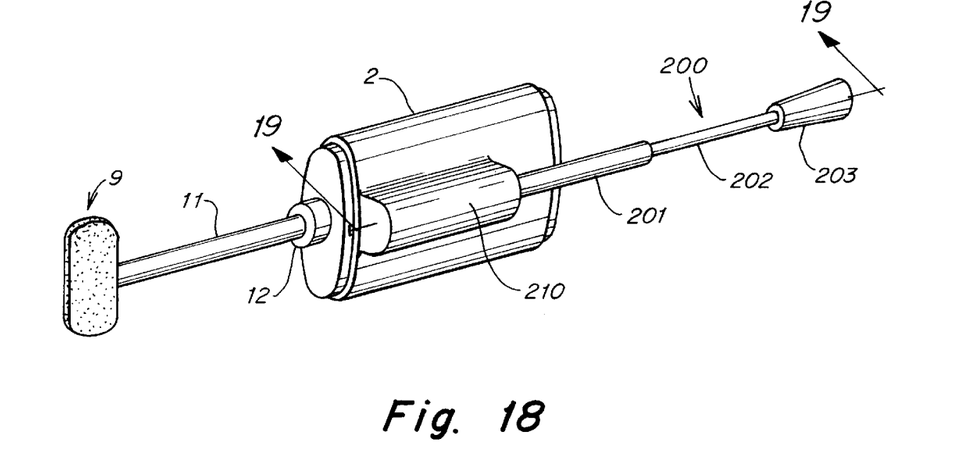
FIG. 18 is a perspective view of another bottle according to the present invention, with the handle and applicator in an extended, operative position.

FIG. 18 shows a further modified arrangement of the present invention which comprises a telescoping tubular rod member 11 which has a head 9 at an end thereon, and which is slidably mounted within the container 2, in a manner similar to that shown in FIGS. 1–5. The rod 11 and its associated head 9, as well as its interconnection to the container 2, may be in accordance with any of the embodiments described hereinabove.

Figure 19:
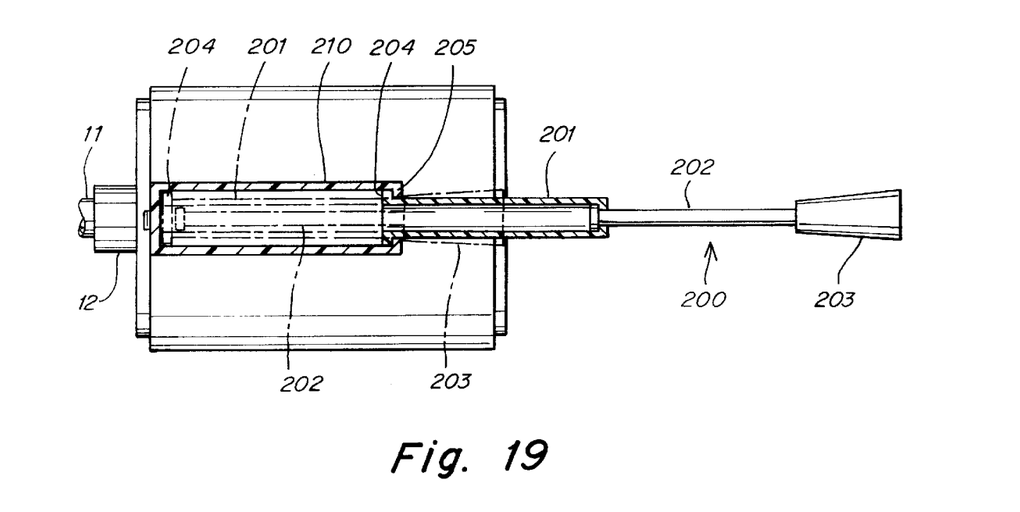
FIG. 19 is a partial longitudinal sectional view of the bottle of FIG. 18, showing the applicator retracted in the bottle and showing the extendible handle in two different positions.

The embodiment of FIG. 18 further comprises a projecting portion 210 of the container 2 which accommodates a telescoping extendible handle member which improves handling of the apparatus and which provides a longer reach in use. The extendible handle comprises a telescoping arrangement 200 which includes an outer telescoping rod-like member 201 which is slidably mounted within housing portion 210, and an inner telescoping portion 202 which is slidably mounted within the outer telescoping portion 201. A handle 203 is provided at the end of telescoping portion 202. FIG. 18 shows the extended handle. FIG. 19 shows the handle in its extended state in solid lines, and in its collapsed position in phantom lines. The outer telescoping member 201 has a projection 204 at the end thereof which cooperates with a stop portion 205 at the end of housing 210, to prevent the outer telescoping member 201 from being disengaged from housing portion 210. The housing portion 210 is preferably molded integrally with the container 2, or it may be made separately and be attached to the container 2, for example by adhesive, solvent or ultrasonic, or other suitable connection technique.

In the embodiment of FIGS. 18 and 19, when the rod 11 is fully extended, and the handle 200 is fully extended, a large extension is obtained, thereby facilitating use. The rod 11 may be a two-part telescoping rod as shown in FIGS. 16 and 17, or a single member unit as shown.

While the invention has been described above with respect to specific embodiments and implementations, it should be clear that various modifications can be made and that the features of the various embodiments can be interchanged and/or combined in any combination consistent with proper operation, within the scope of the invention as defined in the appended claims.

We claim:

1. A bottle for storing a fluid and for applying the fluid to a human body, said bottle comprising:

a container having an opening;

an elongated rod member having a longitudinal axis, said rod member being located in said opening, and said rod member being slidable along its longitudinal axis relative to said container and being sealed against said container so that an inner end of the rod member is located within the container and an outer end of the rod member is located outside the container;

said rod member having a duct extending at least partially in the direction of the longitudinal axis of the rod member, said duct forming a fluid connection between an outlet at said outer end of the rod member and an orifice that is situated at an inner end portion of the rod member which is within the container; and an applicator movably mounted at the outer end of the rod member between a first closure position and a second open position, said applicator having an applicator member that is permeable for the fluid and being in fluid communication with the outlet of the duct when the applicator is in the second open position and being out of fluid communication with the outlet of the duct when the applicator is in the first closure positions; and said orifice of said rod member being spaced from a wall of said container when said rod member is fully retracted within said container such that fluid can flow to said applicator member via said orifice and said duct when said applicator is in said second open position, regardless of whether said rod member is retracted fully into said container or extended from said container.

2. The bottle according to claim 1, further comprising a valve for selectively closing said duct of said rod member when said applicator is moved to said first closure position and opening said duct of said rod member when said applicator is moved to said second open position.

3. The bottle according to claim 2, wherein said valve includes a first portion formed at the outer end of said rod member and a second portion formed by said applicator, said second portion cooperating with said first portion during movement of said applicator.

4. The bottle according to claim 3, wherein said first portion has a first surface and said second portion has a second surface in contact with said first surface, and said first surface is slidable relative to said second surface when said applicator is moved between said first closure position and said second open position.

5. The bottle according to claim 4, wherein said first portion includes a socket formed at the outer end of said rod member and said second portion includes a ball formed on said applicator and rotatably held within said socket, said ball including a passage to permit fluid flow from said duct to said applicator member when said applicator is moved to said second open position and which passage is blocked when said applicator is moved to said first closed position.

6. The bottle according to claim 1, wherein said container has a neck through which said rod member is slidable, and said neck includes a seal which seals said neck relative to said rod member while permitting relative movement between said neck and said rod member.

7. The bottle according to claim 6, wherein said seal includes a wiper acting upon an outer surface of said rod member.

8. The bottle according to claim 1, further comprising detention means for retaining said rod member in at least one longitudinal position relative to said container.

9. The bottle according to claim 1, further comprising a removable cap which is removably engageable with said container to cover said applicator.

* * * * *